(12) United States Patent
Macko et al.

(10) Patent No.: US 11,357,937 B2
(45) Date of Patent: Jun. 14, 2022

(54) COLLAPSIBLE FIBER MATRIX RESERVOIR FOR AN E-VAPING DEVICE

(71) Applicant: Altria Client Services LLC, Richmond, VA (US)

(72) Inventors: Jason Andrew Macko, Richmond, VA (US); Peter Lipowicz, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 252 days.

(21) Appl. No.: 15/226,420

(22) Filed: Aug. 2, 2016

(65) Prior Publication Data

US 2018/0035713 A1 Feb. 8, 2018

(51) Int. Cl.
*A24F 47/00* (2020.01)
*H05B 1/02* (2006.01)
(Continued)

(52) U.S. Cl.
CPC ............ *A61M 15/06* (2013.01); *A24F 40/42* (2020.01); *A61M 11/042* (2014.02);
(Continued)

(58) Field of Classification Search
CPC ........ A24F 47/008; A24F 40/42; A24F 40/10; H05B 3/44; H05B 1/0297;
(Continued)

(56) References Cited

U.S. PATENT DOCUMENTS 2,965,102 A * 12/1960 Harwood ................ A61F 13/47
604/366
3,067,747 A * 12/1962 Wink ...................... C08L 67/02
604/366
3,081,514 A * 3/1963 Griswold ............... D04H 1/736
442/337

(Continued)

FOREIGN PATENT DOCUMENTS

CN 1539036 A 10/2004
CN 201379072 Y 1/2010
(Continued)

OTHER PUBLICATIONS

International Search Report and Written Opinion dated Oct. 20, 2017 for corresponding International Application No. PCT/EP2017/069564.

(Continued)

*Primary Examiner* — Eric S Stapleton
(74) *Attorney, Agent, or Firm* — Harness, Dickey & Pierce, P.L.C.

(57) ABSTRACT

Example embodiments relate to a cartridge configured to house a pre-vapor formulation for an e-vaping device, the cartridge including an inner portion and an outer portion configured to store the pre-vapor formulation. The outer portion includes a plurality of fibers configured to be mobile and/or configured to be substantially free of entanglement with one another. The fibers are configured to be substantially free of entanglement with one another based on the lengths of the plurality of fibers. For example, the lengths of (Continued)

the plurality of fibers may be in a range of about 3 mm to about 7 mm. The lengths may also be about 5 mm.

12 Claims, 7 Drawing Sheets

(51) Int. Cl.
*H05B 3/44* (2006.01)
*A61M 15/06* (2006.01)
*A61M 11/04* (2006.01)
*A24F 40/42* (2020.01)
*A61M 16/00* (2006.01)
*A24F 40/10* (2020.01)

(52) U.S. Cl.
CPC ............. *H05B 1/0297* (2013.01); *H05B 3/44* (2013.01); *A24F 40/10* (2020.01); *A61M 2016/0024* (2013.01); *A61M 2205/587* (2013.01); *A61M 2205/8206* (2013.01)

(58) Field of Classification Search
CPC .............. A61F 13/53409; A61F 13/538; A61F 2013/530167; A61F 13/2068; A61L 15/60; C08L 77/00; Y10S 604/904; A61M 11/042; A61M 15/06; A61M 2205/587; A61M 2205/8206; A61M 2016/0024
USPC ......... 392/403; 604/366–368, 375, 377, 384, 604/904, 90
See application file for complete search history.

(56) References Cited

U.S. PATENT DOCUMENTS

| | | | | |
|---|---|---|---|---|
| 3,340,874 A * | 9/1967 | Burgeni | ............. | A61F 13/2068 604/379 |
| 3,430,630 A * | 3/1969 | Barton | ................. | A61F 13/533 604/365 |
| 3,490,103 A * | 1/1970 | Asaka | ................. | C08L 1/02 28/105 |
| 3,575,173 A * | 4/1971 | Loyer | ............... | A61F 13/15211 604/364 |
| 3,628,534 A * | 12/1971 | Donohue | ................. | A61L 15/60 604/366 |
| 3,663,348 A * | 5/1972 | Liloia | ..................... | D21H 5/26 428/171 |
| 3,804,092 A * | 4/1974 | Tunc | ................. | A61L 15/28 604/364 |
| 3,971,379 A * | 7/1976 | Chatterjee | ............... | A61F 13/00 604/368 |
| 4,002,171 A * | 1/1977 | Taft | ......................... | A61L 15/26 604/364 |
| 4,793,366 A * | 12/1988 | Hill | ..................... | A61K 9/007 131/273 |
| 4,800,903 A * | 1/1989 | Ray | ..................... | A24F 47/002 131/273 |
| 4,813,437 A * | 3/1989 | Ray | ....................... | A24F 42/20 131/273 |
| 4,872,870 A * | 10/1989 | Jackson | ................ | A61F 13/514 604/366 |
| 4,922,901 A * | 5/1990 | Brooks | ................. | A24F 47/008 128/203.26 |
| 4,947,874 A * | 8/1990 | Brooks | ................. | A24F 40/46 131/329 |
| 4,947,875 A * | 8/1990 | Brooks | ................. | A24F 47/006 131/330 |
| 5,509,430 A * | 4/1996 | Berger | ................. | A24D 3/065 131/341 |
| 5,868,724 A * | 2/1999 | Dierckes, Jr. | ..... | A61F 13/15658 604/368 |
| 6,041,789 A * | 3/2000 | Bankert | ................. | A24F 42/20 131/270 |
| 6,761,955 B2 * | 7/2004 | Mizutani | ............. | A61F 13/4752 428/126 |
| 7,521,493 B2 * | 4/2009 | Frances | .................... | H01B 1/24 523/220 |
| 7,726,320 B2 * | 6/2010 | Robinson | ................ | A24F 40/42 131/200 |
| 7,832,410 B2 * | 11/2010 | Hon | ........................ | A24F 40/42 131/273 |
| 8,079,371 B2 * | 12/2011 | Robinson | ............... | A24D 1/002 131/200 |
| 8,375,957 B2 * | 2/2013 | Hon | ....................... | A24F 47/004 131/194 |
| 8,613,284 B2 * | 12/2013 | Hutchens | ............... | A24D 3/068 131/341 |
| 8,899,238 B2 * | 12/2014 | Robinson | ............... | A24B 13/02 131/200 |
| 9,974,334 B2 * | 5/2018 | Dooly | ................... | A24F 40/485 |
| 2002/0029026 A1 * | 3/2002 | Furuya | ................ | A61F 13/5633 604/385.01 |
| 2002/0040210 A1 * | 4/2002 | Luccio | .................... | A61L 15/60 604/367 |
| 2002/0081930 A1 * | 6/2002 | Jackson | ................... | C08L 33/08 442/416 |
| 2004/0131820 A1 * | 7/2004 | Turner | ................... | B32B 5/022 428/92 |
| 2004/0265534 A1 * | 12/2004 | Curro | ....................... | A61Q 5/02 428/92 |
| 2005/0177122 A1 * | 8/2005 | Berba | ................... | A61F 13/537 604/367 |
| 2008/0092912 A1 * | 4/2008 | Robinson | ............... | A24B 13/02 131/200 |
| 2008/0167634 A1 * | 7/2008 | Kouta | ............... | A61F 13/53409 604/367 |
| 2008/0302375 A1 * | 12/2008 | Andersson | .............. | A24F 40/42 131/273 |
| 2010/0200006 A1 * | 8/2010 | Robinson | ................. | A24B 3/14 131/194 |
| 2010/0310845 A1 * | 12/2010 | Bond | .................. | A61F 13/5376 428/219 |
| 2012/0060853 A1 * | 3/2012 | Robinson | ............... | A24D 1/002 131/191 |
| 2012/0285476 A1 * | 11/2012 | Hon | ..................... | H05B 3/0004 131/329 |
| 2013/0123409 A1 * | 5/2013 | Clark | ....................... | D01F 8/06 524/315 |
| 2013/0133856 A1 * | 5/2013 | D'Herbecourt | .......... | D01F 6/82 165/46 |
| 2013/0192615 A1 * | 8/2013 | Tucker | .................. | A24F 47/004 131/328 |
| 2014/0238424 A1 * | 8/2014 | Macko | .................... | A24F 40/44 131/328 |
| 2014/0261486 A1 * | 9/2014 | Potter | .................... | A24F 40/30 131/328 |
| 2014/0261487 A1 * | 9/2014 | Chapman | ............... | A24F 47/008 131/328 |
| 2015/0034103 A1 * | 2/2015 | Hon | ........................ | A24F 47/00 131/328 |
| 2015/0040930 A1 * | 2/2015 | Robinson | ................ | A24F 40/42 131/329 |
| 2015/0047656 A1 * | 2/2015 | Robinson | ................ | A24D 1/20 131/275 |
| 2015/0201674 A1 * | 7/2015 | Dooly | ................... | A24F 40/42 53/432 |
| 2016/0074569 A1 | 3/2016 | Schuetz et al. | | |
| 2016/0120224 A1 * | 5/2016 | Mishra | .................. | A24F 47/008 392/390 |
| 2017/0020200 A1 * | 1/2017 | Robinson | ................ | A24B 13/02 |

FOREIGN PATENT DOCUMENTS

| | | |
|---|---|---|
| CN | 103179870 A | 6/2013 |
| CN | 204540821 U | 8/2015 |
| EA | 023394 B1 | 12/2012 |
| EP | 2550879 A1 | 1/2013 |

(56) References Cited

FOREIGN PATENT DOCUMENTS

| KR | 10-2012-0132004 A | 12/2012 |
|----|------------------|---------|
| RU | 110608 U1 | 11/2011 |
| RU | 2621596 C2 | 6/2017 |
| WO | WO-2006101061 A1 | 9/2006 |
| WO | WO-2014130692 A1 | 8/2014 |
| WO | WO-2016/054476 A1 | 4/2016 |

OTHER PUBLICATIONS

Notice of Allowance for corresponding Russian Application No. 2019103838/12(007225) dated Nov. 12, 2020.
International Search Report dated Apr. 6, 2021 for corresponding Chinese Patent Application No. 201780042656.1.
Japanese Office Action dated Jul. 5, 2021 for corresponding Japanese Patent Application No. 2019-503665.

* cited by examiner

Empty

FIG. 8

COLLAPSIBLE FIBER MATRIX RESERVOIR FOR AN E-VAPING DEVICE

BACKGROUND OF THE INVENTION

Field of the Invention

Example embodiments relate generally to a pre-vapor formulation reservoir for an e-vaping device, to a reservoir configured to increase the amount of heated pre-vapor formulation, and/or to a method of increasing the useful lifetime of an e-vaping device cartridge.

Related Art

Electronic vaping devices are used to vaporize a pre-vapor formulation into a vapor in order for an adult vapor to draw the vapor through one or more outlets of the device. These electronic vaping devices may be referred to as e-vaping devices. An e-vaping device may typically include several e-vaping elements such as a power supply section and/or a cartridge. The power supply section may include a battery, and the cartridge may include a heater along with a reservoir capable of storing the pre-vapor formulation. The reservoir may include a winding of cotton or cellulose gauze or other fibrous material about an inner tube or about a portion of the reservoir. The cartridge may include the heater in communication with the pre-vapor formulation via a wick, the heater being configured to heat the pre-vapor formulation at the wick to produce a vapor. The pre-vapor formulation may include an amount of nicotine as well as a vapor former and possibly water, acids, flavorants and/or aromas. The pre-vapor formulation may include a material or combination of materials that may be transformed into a vapor. For example, the pre-vapor formulation may include a liquid, solid and/or gel formulation including, but not limited to, water, beads, solvents, active ingredients, ethanol, plant extracts, natural or artificial flavors, and/or vapor formers such as glycerine and/or propylene glycol.

In e-vaping devices, the pre-vapor formulation included in the reservoir may be in free flowing form and may be kept in place with a cylindrical gauze surrounding the pre-vapor formulation, which may result in an amount of pre-vapor formulation being wasted. For example, about 40% of the pre-vapor formulation may remain in the reservoir and is not transferred to the wick to be heated during operation of the e-vaping device.

SUMMARY OF THE INVENTION

At least one example embodiment relates to a cartridge of an e-vaping device including insoluble polymer fibers configured to store a pre-vapor formulation solution.

In at least one example embodiment, the reservoir of an e-vaping device may include a winding of inner and outer fibrous material about an inner tube or about a portion of the reservoir. For example, the inner fibrous material and the outer fibrous material such as, for example, cotton gauze and/or insoluble polymer fibers, may store a pre-vapor formulation. For example, the polymer fibers may be chemically compatible with the various ingredients of the pre-vapor formulation, e.g., the polymer fibers may be substantially chemically inert in the presence of the various ingredients of the pre-vapor formulation. The polymer fibers may include, for example, a polypropylene core with, for example, an ethylene vinylacetate sheath. The polymer fibers may be added to the pre-vapor formulation solution and stirred so as to be substantially evenly distributed in the pre-vapor formulation solution.

In at least one example embodiment, the polymer fibers are added in an amount that is sufficient to substantially absorb or soak the pre-vapor formulation solution. For example, the amount of polymer fibers is sufficient to substantially retain the pre-vapor formulation solution without leakage. In example embodiments, the pre-vapor formulation solution is retained in interstitial spaces between the fibers. As a result, a liquid suspension, which is a heterogeneous mixture containing the polymer fibers and the pre-vapor formulation solution where the polymer fibers are capable of sedimentation, is created in the reservoir. As a result, due to the presence of the polymer fibers, the liquid suspension may inhibit the flow of the pre-vapor formulation solution, and the pre-vapor formulation solution may thus be impeded or prevented from inadvertently flowing out of the reservoir of the e-vaping device.

In example embodiments, the polymer fibers may be distributed in the outer gauze of the reservoir. For example, the polymer fibers include the pre-vapor formulation in suspension and are sufficiently short to allow mobility of the fibers within the reservoir and avoid entanglement with other fibers, and thus to allow improved drainage of the pre-vapor formulation to the wick within the reservoir. The fibers become mobile within the reservoir by capillary action when the e-vaping device is in operation and air is drawn in the e-vaping device. In addition, by using the pre-vapor formulation in suspension in the polymer fibers, the outer gauze typically used in other e-vaping devices may be omitted, which may lead to lower manufacturing costs. In example embodiments, the concentration of the polymer fibers in the reservoir may be less than about 4% by weight.

Example embodiments relate to a cartridge configured to house a pre-vapor formulation for an e-vaping device, the cartridge including an inner portion and an outer portion configured to store the pre-vapor formulation. The outer portion includes a plurality of fibers configured to be mobile and/or configured to be substantially free of entanglement with one another as a result of the short lengths of the fibers. The inner portion may include a high-density gauze. In example embodiments, the fibers become mobile through capillary action when the e-vaping device is in operation and air is drawn in the e-vaping device.

In example embodiments, the plurality of fibers are configured to both retain enough pre-vapor formulation and be substantially free of entanglement with one another based on the respective lengths of the plurality of fibers. For example, the respective lengths of the plurality of fibers may be in a range of about 3 mm to about 7 mm. In example embodiments, if the respective lengths of the fibers are shorter than about 3 mm, the fibers may cluster at one or more fixed locations of the reservoir, such as the side of the reservoir that is closest to the battery of the e-vaping device, and may thus not sufficiently retain the pre-vapor formulation, resulting in possible loss of the pre-vapor formulation via leakage. If the respective lengths of the fibers are longer than about 7 mm, then the fibers may entangle with other fibers and would become less mobile as a result, and the pre-vapor formulation, during operation of the e-vaping device, would be impeded from flowing from the outer portion of the reservoir to the inner portion of the reservoir and to the wick so as to be heated by the heater. The respective lengths of the plurality of fibers may also be, for example, about 5 mm.

In example embodiments, about 30% of the plurality of fibers have a length of about 3 mm, about 50% of the plurality of fibers have a length of about 5 mm, and about 20% of the plurality of fibers have a length of about 7 mm. In other example embodiments, about 20% of the plurality of fibers have a length of about 3 mm, about 75% of the plurality of fibers have a length of about 5 mm, and about 5% of the plurality of fibers have a length of about 7 mm. In other example embodiments, about 30% of the plurality of fibers have a length of about 3 mm, about 60% of the plurality of fibers have a length of about 5 mm, and about 10% of the plurality of fibers have a length of about 7 mm.

In example embodiments, the respective diameters of the plurality of fibers are in a range of about 20 μm to about 28 μm. In example embodiments, if the respective diameters of the fibers are outside of the above range, which is smaller than about 20 μm or greater than about 28 μm, then the fibers may either be prevented from sufficiently retaining the pre-vapor formulation, or be less mobile because of entanglement with other fibers. As a result, the fibers would be less mobile and the flow of the pre-vapor formulation would be impeded from flowing from the outer portion of the reservoir to the inner portion of the reservoir and to the wick so as to be heated by the heater during operation of the e-vaping device. For example, the diameter of the plurality of fibers may be about 24 μm.

In example embodiments, the surface areas of the plurality of fibers are in a range of about 13 $in^2$ to about 17 $in^2$. In example embodiments, if the respective surface areas of the fibers are outside of the above range, which is smaller than about 13 $in^2$ or greater than about 17 $in^2$, then the fibers may either be prevented from sufficiently retaining the pre-vapor formulation, or be less mobile because of entanglement with other fibers. As a result, the fibers would be less mobile and the flow of the pre-vapor formulation would be impeded from flowing from the outer portion of the reservoir to the inner portion of the reservoir and to the wick so as to be heated by the heater during operation of the e-vaping device. For example, the surface area of each of the plurality of fibers may be about 15 $in^2$.

An example method of manufacturing an e-vaping device includes mixing a pre-vapor formulation solution with polymer fibers so that the fibers are distributed substantially homogeneously in the pre-vapor formulation solution to form a suspension, and injecting the suspension in the reservoir of the e-vaping device. In example embodiments, the pre-vapor formulation solution including the polymer fibers may be prepared separately and subsequently injected as a suspension in the reservoir of the e-vaping device.

In example embodiments, when the suspension of the pre-vapor formulation solution and polymer fibers is in contact with the wick of the e-vaping device, the wick may absorb the liquid from the pre-vapor formulation suspension, and operation of the e-vaping device may be carried out.

In example embodiments, flavors, acids and/or aromas or other ingredients may be included in the pre-vapor formulation suspension.

As a result of including polymer fibers in the pre-vapor formulation solution to form a solution, the useful lifetime of the cartridge of an e-vaping device may be increased compared to other e-vaping devices that do not include polymer fibers in suspension in the pre-vapor formulation solution. For example, a larger proportion of the solution may be stored in the fibers due to a better distribution of the fibers in the reservoir, and the solution stored in the fibers is more efficiently transferred to and absorbed by the wick during operation of the e-vaping device because of the mobility of the fibers in the pre-vapor formulation solution.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section, Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations and/or elements, but do not preclude the presence or addition of one or more other features, integers, steps, operations, elements and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments. The same reference numerals represent the same elements throughout the drawings.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

As used herein, the term "vapor former" describes any suitable known compound or mixture of compounds that, in use, facilitates formation of a vapor and that is substantially resistant to thermal degradation at the operating temperature of the vapor-generating device. Suitable vapor-formers consist of various compositions of polyhydric alcohols such as propylene glycol. In at least one embodiment, the vapor former is propylene glycol.

Figure 1:
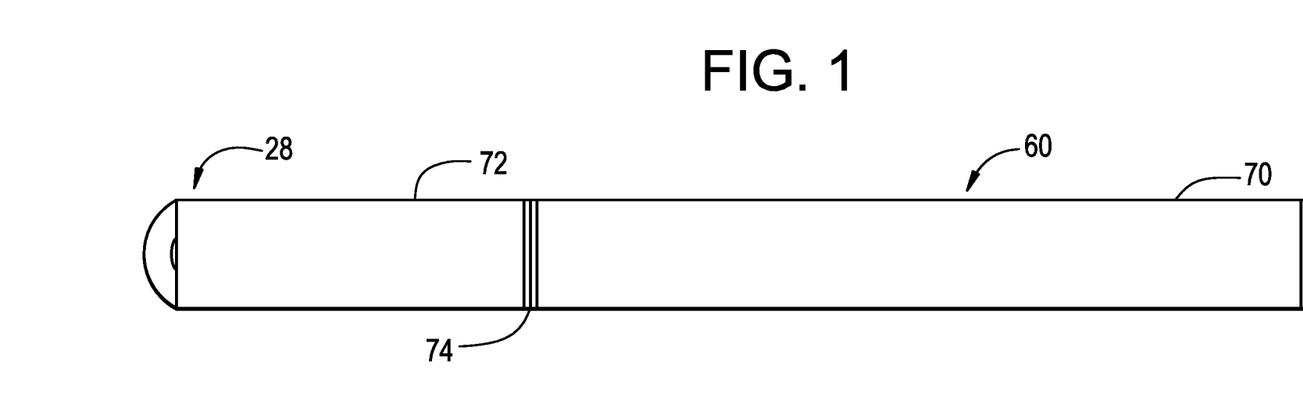
FIG. 1 is a side view of an e-vaping device, according to an example embodiment.

FIG. 1 is a side view of an e-vaping device or a "cigalike" device 60, according to an example embodiment. In FIG. 1, the e-vaping device 60 includes a first section or cartridge 70 and a second section 72, which are coupled together at a threaded joint 74 or by other connecting structure such as a snug-fit, snap-fit, detent, clamp and/or clasp or the like. In at least one example embodiment, the first section or cartridge 70 may be a replaceable cartridge, and the second section 72 may be a reusable section. Alternatively, the first section or cartridge 70 and the second section 72 may be integrally formed in one piece. In at least one embodiment, the second section 72 includes a LED at a distal end 28 thereof.

Figure 2:
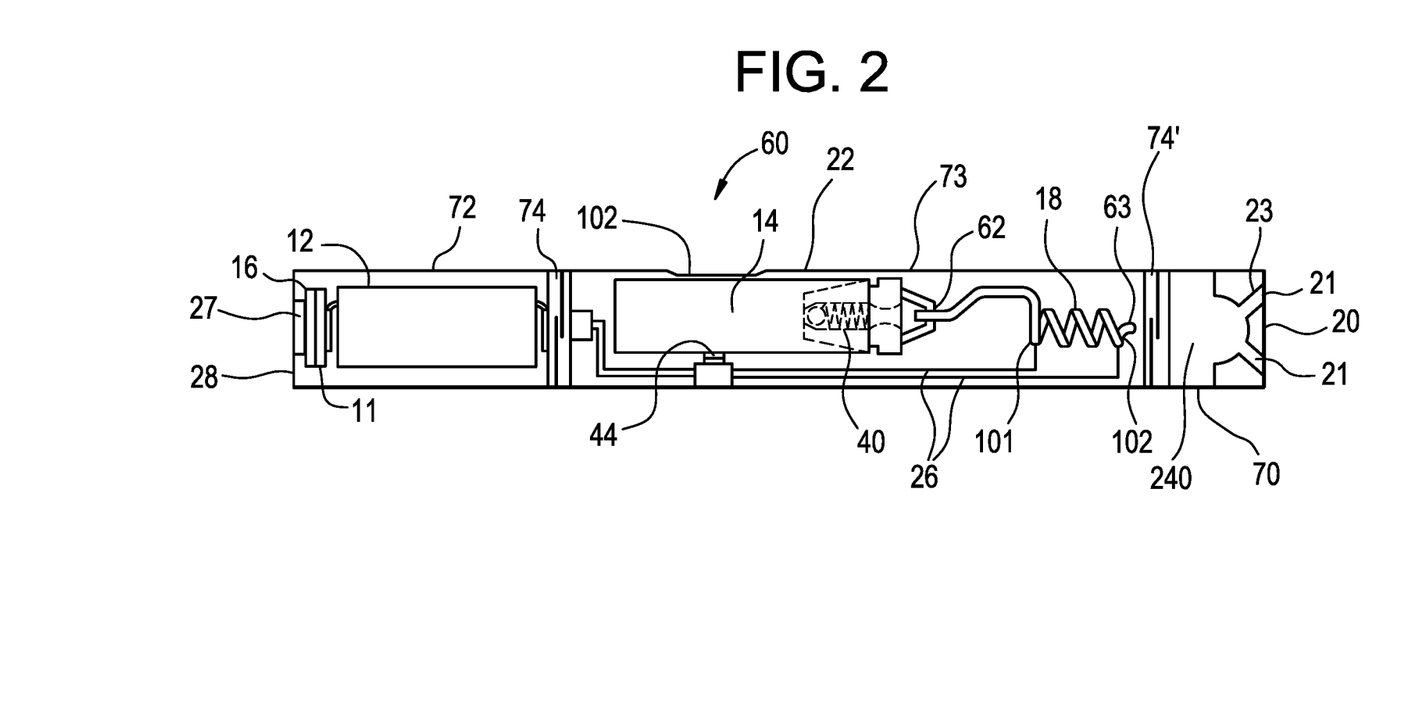
FIG. 2 is a longitudinal cross-sectional view of an e-vaping device, according to an example embodiment.

FIG. 2 is a cross-sectional view of an example embodiment of an e-vaping device. As shown in FIG. 2, the first section or cartridge 70 can house a mouth-end insert 20, a capillary capillary tube 18, and a reservoir 14.

In example embodiments, the reservoir 14 may include a wrapping of gauze about an inner tube (not shown). For example, the reservoir 14 may be formed of or include an outer wrapping of gauze surrounding an inner wrapping of gauze. In at least one example embodiment, the reservoir 14 may be formed of or include an alumina ceramic in the form of loose particles, loose fibers, or woven or nonwoven fibers. Alternatively, the reservoir 14 may be formed of or include a cellulosic material such as cotton or gauze material, or a polymer material, such as polyethylene terephthalate, in the form of a bundle of loose fibers. A more detailed description of the reservoir 14 is provided below.

The second section 72 can house a power supply 12, control circuitry 11 configured to control the power supply 12, and a puff sensor 16. The puff sensor 16 is configured to sense when an adult vaper is drawing on the e-vaping device 60, which triggers operation of the power supply 12 via the control circuitry 11 to heat the pre-vapor formulation housed in the reservoir 14, and thereby form a vapor. A threaded portion 74 of the second section 72 can be connected to a battery charger, when not connected to the first section or cartridge 70, to charge the battery or power supply section 12.

In example embodiments, the capillary tube 18 is formed of or includes a conductive material, and thus may be configured to be its own heater by passing current through the tube 18. The capillary tube 18 may be any electrically conductive material capable of being heated, for example resistively heated, while retaining the necessary structural integrity at the operating temperatures experienced by the capillary tube 18, and which is non-reactive with the pre-vapor formulation. Suitable materials for forming the capillary tube 18 are one or more of stainless steel, copper, copper alloys, porous ceramic materials coated with film resistive material, nickel-chromium alloys, and combinations thereof. For example, the capillary tube 18 is a stainless steel capillary tube 18 and serves as a heater via electrical leads 26 attached thereto for passage of direct or alternating current along a length of the capillary tube 18. Thus, the stainless steel capillary tube 18 is heated by, for example, resistance heating. Alternatively, the capillary tube 18 may be a non-metallic tube such as, for example, a glass tube. In such an embodiment, the capillary tube 18 also includes a conductive material such as, for example, stainless steel, nichrome or platinum wire, arranged along the glass tube and capable of being heated, for example resistively. When the conductive material arranged along the glass tube is heated, pre-vapor formulation present in the capillary tube 18 is heated to a temperature sufficient to at least partially volatilize pre-vapor formulation in the capillary tube 18.

In at least one embodiment, the electrical leads 26 are bonded to the metallic portion of the capillary tube 18. In at least one embodiment, one electrical lead 26 is coupled to a first, upstream portion 101 of the capillary tube 18 and a second electrical lead 26 is coupled to a downstream, end portion 102 of the capillary tube 18.

In operation, when an adult vaper draws on the e-vaping device, the puff sensor 16 detects a pressure gradient caused by the drawing of the adult vaper, and the control circuitry 11 controls heating of the pre-vapor formulation located in the reservoir 14 by providing power to the capillary tube 18. Once the capillary tube 18 is heated, the pre-vapor formulation contained within a heated portion of the capillary tube 18 is volatilized and emitted from the outlet 63, where the pre-vapor formulation expands and mixes with air and forms a vapor in mixing chamber 240.

As shown in FIG. 2, the reservoir 14 includes a valve 40 configured to maintain the pre-vapor formulation within the reservoir 14 and to open when the reservoir 14 is squeezed and pressure is applied thereto, the pressure being created when an adult vaper draws on the e-vaping device at the mouth-end insert 20, which results in the reservoir 14 forcing the pre-vapor formulation through the outlet 62 of the reservoir 14 to the capillary tube 18. In at least one embodiment, the valve 40 opens when a critical, minimum pressure is reached so as to avoid inadvertently dispensing pre-vapor formulation from the reservoir 14. In at least one embodiment, the pressure required to press the pressure switch 44 is high enough such that accidental heating due to the pressure switch 44 being inadvertently pressed by outside factors such as physical movement or collision with outside objects is avoided.

The power supply 12 of example embodiments can include a battery arranged in the second section 72 of the e-vaping device 60. The power supply 12 is configured to apply a voltage to volatilize the pre-vapor formulation housed in the reservoir 14.

In at least one embodiment, the electrical connection between the capillary tube 18 and the electrical leads 26 is substantially conductive and temperature resistant while the capillary tube 18 is substantially resistive so that heat generation occurs primarily along the capillary tube 18 and not at the contacts.

The power supply section or battery 12 may be rechargeable and include circuitry allowing the battery to be chargeable by an external charging device. In example embodiments, the circuitry, when charged, provides power for a given number of draws through outlets of the electronic vaping device, after which the circuitry may have to be re-connected to an external charging device.

In at least one embodiment, the e-vaping device 60 may include control circuitry 11 which can be, for example, on a printed circuit board. The control circuitry 11 may also include a heater activation light 27 that is configured to glow when the device is activated. In at least one embodiment, the heater activation light 27 comprises at least one LED and is at a distal end 28 of the e-vaping device 60 so that the heater activation light 27 illuminates a cap which takes on the appearance of a burning coal during a draw through outlets of the electronic vaping device. Moreover, the heater activation light 27 can be configured to be visible to the adult vaper. The light 27 may also be configured such that the adult vaper can activate and/or deactivate the light 27 when desired, such that the light 27 is not activated during vaping if desired.

In at least one embodiment, the e-vaping device 60 further includes a mouth-end insert 20 having at least two off-axis, diverging outlets 21 that are uniformly distributed around the mouth-end insert 20 so as to substantially uniformly distribute vapor in an adult vaper's mouth during operation of the e-vaping device. In at least one embodiment, the mouth-end insert 20 includes at least two diverging outlets 21 (e.g., 3 to 8 outlets or more). In at least one embodiment, the outlets 21 of the mouth-end insert 20 are located at ends of off-axis passages 23 and are angled outwardly in relation to the longitudinal direction of the e-vaping device 60 (e.g., divergently). As used herein, the term "off-axis" denotes an angle to the longitudinal direction of the e-vaping device.

In at least one embodiment, the e-vaping device 60 is about the same size as a tobacco-based product. In some embodiments, the e-vaping device 60 may be about 80 mm to about 110 mm long, for example about 80 mm to about 100 mm long and about 7 mm to about 10 mm in diameter.

The outer cylindrical housing 22 of the e-vaping device 60 may be formed of or include any suitable material or combination of materials. In at least one embodiment, the outer cylindrical housing 22 is formed at least partially of metal and is part of the electrical circuit connecting the control circuitry 11, the power supply 12 and the puff sensor 16.

As shown in FIG. 2, the e-vaping device 60 can also include a middle section (third section) 73, which can house the pre-vapor formulation reservoir 14 and the capillary tube 18. The middle section 73 can be configured to be fitted with a threaded joint 74' at an upstream end of the first section or cartridge 70 and a threaded joint 74 at a downstream end of the second section 72. In this example embodiment, the first section or cartridge 70 houses the mouth-end insert 20, while the second section 72 houses the power supply 12 and the control circuitry 11 that is configured to control the power supply 12.

Figure 3:
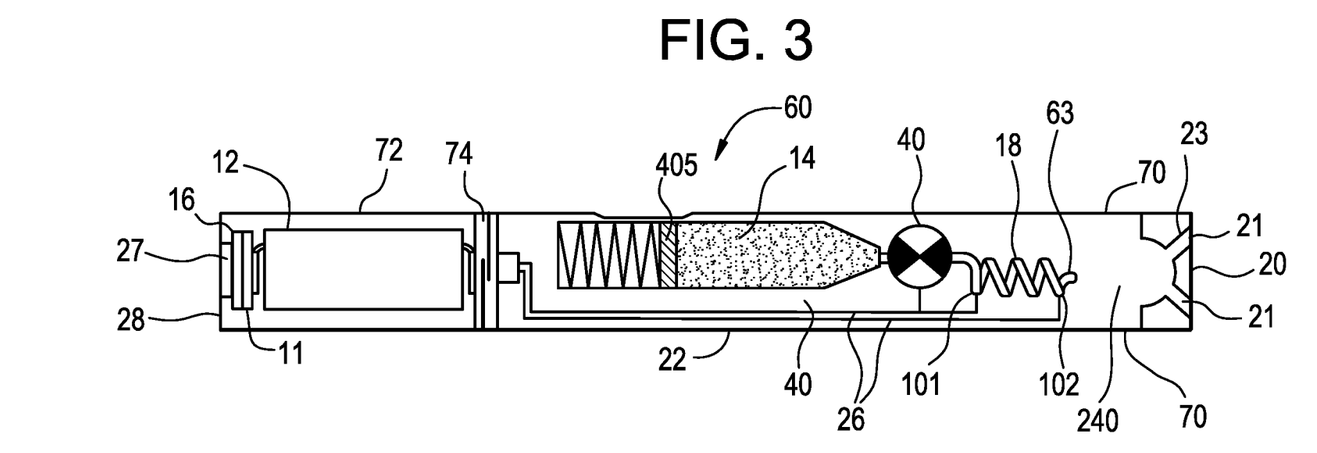
FIG. 3 is a longitudinal cross-sectional of another example embodiment of an e-vaping device.

FIG. 3 is a cross-sectional view of an e-vaping device according to an example embodiment. In at least one embodiment, the first section or cartridge 70 is replaceable so as to avoid the need for cleaning the capillary tube 18. In at least one embodiment, the first section or cartridge 70 and the second section 72 may be integrally formed without threaded connections to form a disposable e-vaping device.

As shown in FIG. 3, in other example embodiments, a valve 40 can be a two-way valve, and the reservoir 14 can be pressurized. For example, the reservoir 14 can be pressurized using a pressurization arrangement 405 configured to apply constant pressure to the reservoir 14. As such, emission of vapor formed via heating of the pre-vapor formulation housed in the reservoir 14 is facilitated. Once pressure upon the reservoir 14 is relieved, the valve 40 closes and the heated capillary tube 18 discharges any pre-vapor formulation remaining downstream of the valve 40.

Figure 4:
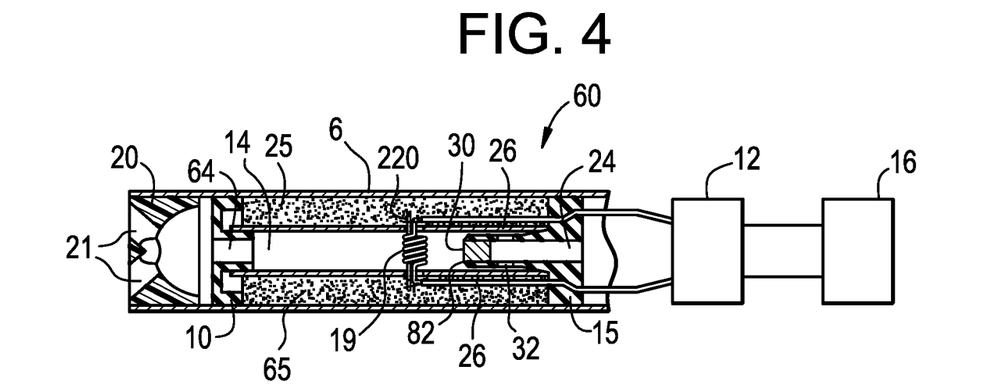
FIG. 4 is a longitudinal cross-sectional view of another example embodiment of an e-vaping device.

FIG. 4 is a longitudinal cross-sectional view of another example embodiment of an e-vaping device. In FIG. 4, the e-vaping device 60 can include a central air passage 24 in an upstream seal 15. The central air passage 24 opens to the inner tube 65. Moreover, the e-vaping device 60 includes a reservoir 14 configured to store the pre-vapor formulation. The reservoir 14 includes the pre-vapor formulation and optionally a storage medium 25 such as gauze configured to store the pre-vapor formulation therein. In an embodiment, the reservoir 14 is contained in an outer annulus between the outer tube 6 and the inner tube 65. The annulus is sealed at an upstream end by the seal 15 and by a stopper 10 at a downstream end so as to prevent leakage of the pre-vapor formulation from the reservoir 14. The heater 19 at least partially surrounds a central portion of a wick 220 such that when the heater is activated, the pre-vapor formulation present in the central portion of the wick 220 is vaporized to form a vapor. The heater 19 is connected to the battery 12 by two spaced apart electrical leads 26. The e-vaping device 60 further includes a mouth-end insert 20 having at least two outlets 21. The mouth-end insert 20 is in fluid communication with the central air passage 24 via the interior of inner tube 65 and a central passage 64, which extends through the stopper 10.

The e-vaping device 60 may include an air flow diverter comprising an impervious plug 30 at a downstream end 82 of the central air passage 24 in seal 15. In at least one example embodiment, the central air passage 24 is an axially extending central passage in seal 15, which seals the upstream end of the annulus between the outer and inner tubes 6, 65. The radial air channel 32 directing air from the central passage 20 outward toward the inner tube 65. In operation, when an adult vaper draws through outlets of the electronic vaping device, the puff sensor 16 detects a pressure gradient caused by the drawing of the adult vaper through outlets of the electronic e-vaping device, and as a result the control circuitry 11 controls heating of the pre-vapor formulation located in the reservoir 14 by providing power the heater 19.

Figure 5A:
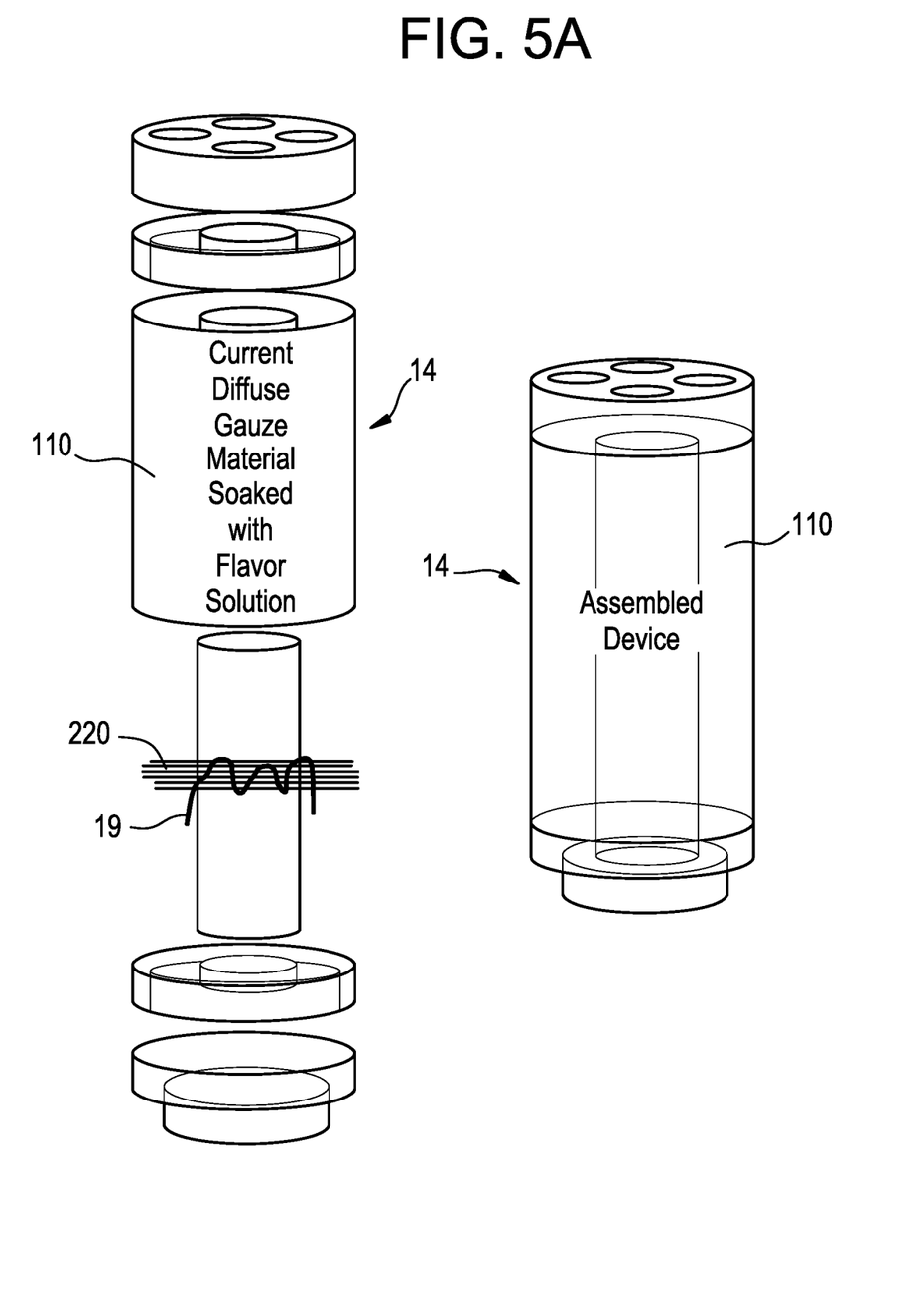
FIG. 5A is a perspective view of a reservoir that does not include a fiber matrix.

FIG. 5A is a perspective view of a reservoir that does not include a fiber matrix. In FIG. 5A, a typical reservoir 14 of an e-vaping device includes a gauze or other fibrous material 110 configured to store the pre-vapor formulation solution, the pre-vapor formulation solution being transmitted to the wick 220 and being heated by the heater 19 during operation of the e-vaping device. Typically, the gauze or fibrous material 110 may be in the form of a winding, and may include an inner gauze that is a high-density gauze, and an outer gauze that is a diffuse gauze. The inner and outer gauze 110 are configured to store the pre-vapor formulation.

Figure 5B:
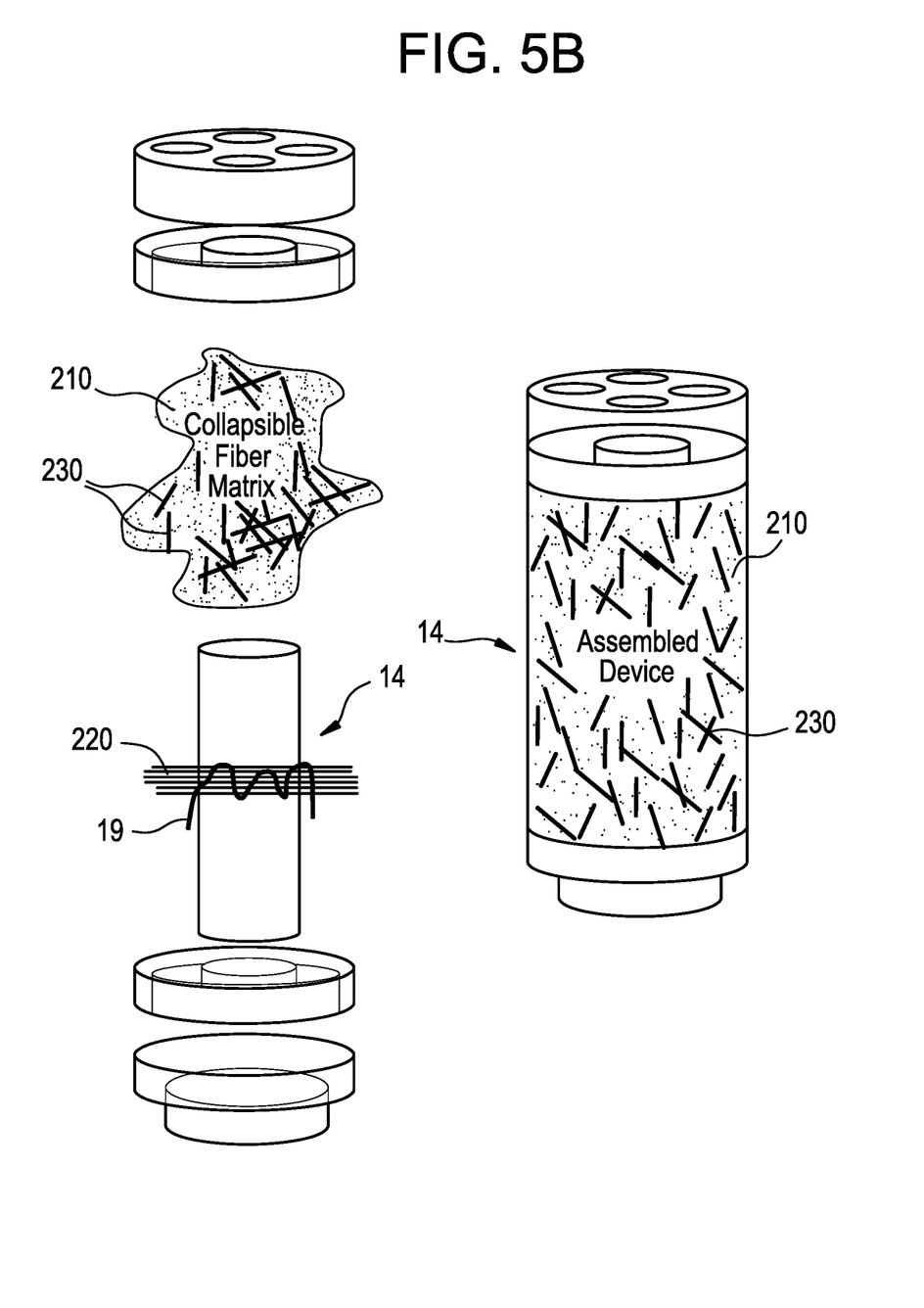
FIG. 5B is a perspective view of a reservoir including a fiber matrix, according to at least one example embodiment.

FIG. 5B is a perspective view of a reservoir including a fiber matrix, according to at least one example embodiment. In FIG. 5B, a reservoir 14 of an e-vaping device includes a gauze or other fibrous material 210 configured to store the pre-vapor formulation solution (not shown), the pre-vapor formulation solution being transferred to the wick 220 to be heated by the heater 19 during operation of the e-vaping device. Typically, the gauze or fibrous material 210 may be in the form of a winding, and may include, for example, a high-density gauze. The gauze 210 may include the pre-vapor formulation. In example embodiments, the gauze 210 includes a matrix of a plurality of fibers 230, which may be insoluble polymer fibers, configured to be substantially free of entanglement with one another based on the lengths of the plurality of fibers 230. Accordingly, the respective lengths of the plurality of fibers 230 are such that entanglement between the fibers 230 is substantially prevented. For example, the lengths of the plurality of fibers 230 may be in a range of about 3 mm to about 7 mm. The lengths of the plurality of fibers 230 may also be about 5 mm. In example embodiments, if the respective lengths of the fibers 230 are shorter than about 3 mm, the fibers 230 may cluster at one or more fixed locations of the reservoir 14, such as the side of the reservoir 14 that is closest to the battery of the e-vaping device (not shown), and may thus not sufficiently retain the pre-vapor formulation, resulting in possible loss of the pre-vapor formulation via leakage. If the respective lengths of the fibers 230 are longer than about 7 mm, then the fibers 230 may entangle with other fibers 230 and may become less mobile as a result, and the pre-vapor formulation, during operation of the e-vaping device, would be impeded from flowing from the outer portion of the reservoir 14 to the inner portion of the reservoir 14 and to the wick 220 so as to be heated by the heater 19.

In example embodiments, about 30% of the plurality of fibers 230 have a length of about 3 mm, about 50% of the plurality of fibers 230 have a length of about 5 mm, and about 20% of the plurality of fibers 230 have a length of about 7 mm. In other example embodiments, about 20% of the plurality of fibers 230 have a length of about 3 mm, about 75% of the plurality of fibers 230 have a length of about 5 mm, and about 5% of the plurality of fibers 230 have a length of about 7 mm. In other example embodiments, about 30% of the plurality of fibers 230 have a length of about 3 mm, about 60% of the plurality of fibers 230 have a length of about 5 mm, and about 10% of the plurality of fibers 230 have a length of about 7 mm.

In example embodiments, the diameter of the plurality of fibers 230 is in a range of about 20 μm to about 28 μm. In example embodiments, if the respective diameters of the fibers 230 are outside of the above range, which is smaller than about 20 μm or greater than about 28 μm, then the fibers 230 may either be prevented from sufficiently retaining the pre-vapor formulation, or be less mobile because of entanglement with other fibers 230. As a result, the fibers 230 would be less mobile and the flow of the pre-vapor formulation would be impeded from flowing from the outer portion of the reservoir 14 to the inner portion of the reservoir 14 and to the wick 220 so as to be heated by the heater 19 during operation of the e-vaping device. For example, the diameter of the plurality of fibers 230 is about 24 μm.

In example embodiments, the surface area of each of the plurality of fibers 230 is in a range of about 13 $in^2$ to about 17 $in^2$. In example embodiments, if the respective surface areas of the fibers 230 are outside of the above range, which is shorter than about 13 $in^2$ or longer than about 17 $in^2$, then the fibers 230 may be less mobile and may entangle with other fibers 230, which would result in less mobility of the fibers 230 and would thus impede the flow of the pre-vapor formulation from the outer portion of the reservoir 14 to the inner portion of the reservoir 14 and to the wick 220 so as to be heated by the heater 19 during operation of the e-vaping device. For example, the surface area of each of the plurality of fibers 230 is about 15 $in^2$.

Figure 6A:
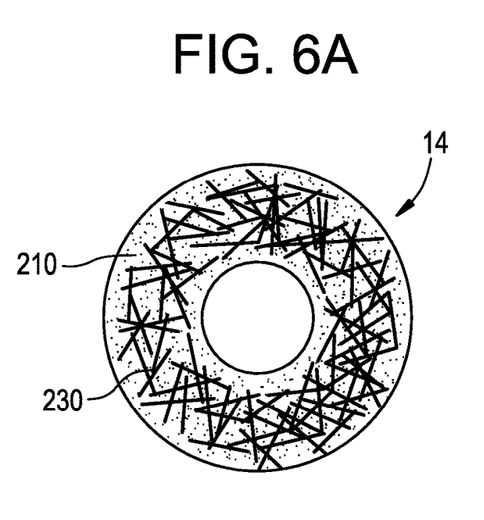
FIGS. 6A and 6B are cross sections of a reservoir including a plurality of fibers, according to at least one example embodiment.
Figure 6B:
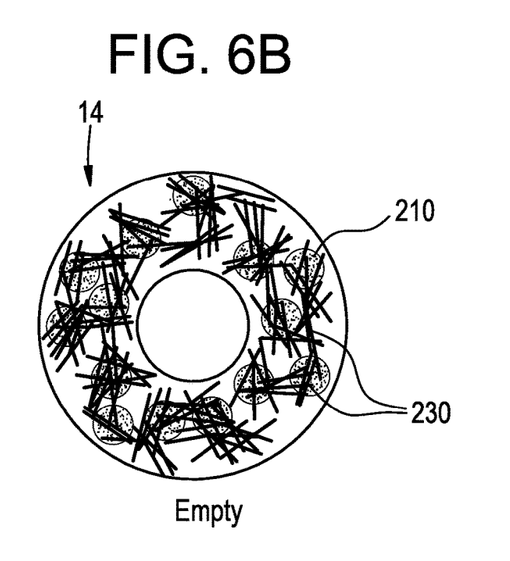

FIGS. 6A and 6B are cross sections of a reservoir including a plurality of fibers in the pre-vapor formulation solution, according to at least one example embodiment. In FIGS. 6A and 6B, which are views of a radial cross-section of a reservoir 14 of an e-vaping device during operation of the e-vaping device. In FIG. 6A, which illustrates the state where the reservoir 14 is substantially full with the pre-vapor formulation solution, the plurality of fibers 230 are substantially homogeneously distributed in the reservoir 14 within the gauze or other fibrous material 210 that is configured to store the pre-vapor formulation solution. When the pre-vapor formulation solution is included in the reservoir 14, substantially all of the pre-vapor formulation solution is absorbed or soaked by the plurality of fibers 230, resulting in a liquid suspension of the pre-vapor formulation solution in the reservoir 14. In example embodiments, the pre-vapor formulation solution is trapped in interstitial spaces between the fibers 230. As a result, the pre-vapor formulation solution is substantially kept in the reservoir 14, and the flow of the pre-vapor formulation solution is substantially prevented from unintentionally draining out of the reservoir 14. Accordingly, waste of pre-vapor formulation solution is reduced or substantially prevented.

FIG. 6B illustrates a state where the pre-vapor formulation solution has been used to a large extent and the reservoir 14 is substantially empty. As a result, the plurality of fibers 230 and the high-density gauze 210 are compressed, resulting in the expression of additional amounts of pre-vapor formulation solution that was previously soaked or absorbed by the plurality of fibers 230. The compression of the plurality of fibers 230 and the high-density gauze 210 is akin to a wringing motion, where residual amounts of the pre-vapor formulation solution previously soaked or absorbed by the plurality of fibers 230 are expelled from the fibers 230 and transferred to the wick (not shown) to be heated by the heater (not shown) and drawn out of the e-vaping device. As a result, more pre-vapor formulation solution is used during operation of the e-vaping device than with an e-vaping device that does not include fibers in the reservoir 14, and waste of the pre-vapor formulation solution is reduced or substantially prevented.

In various example embodiments, the plurality of fibers 230 and the gauze 210 may concentrate radially around the center of the reservoir 14, or may coalesce, as illustrated in FIG. 6B, at one or more locations throughout the reservoir 14. The wringing motion may occur at each of the coalescence locations, resulting in residual pre-vapor formulation solution being expelled from the plurality of fibers 230.

Figure 7A:
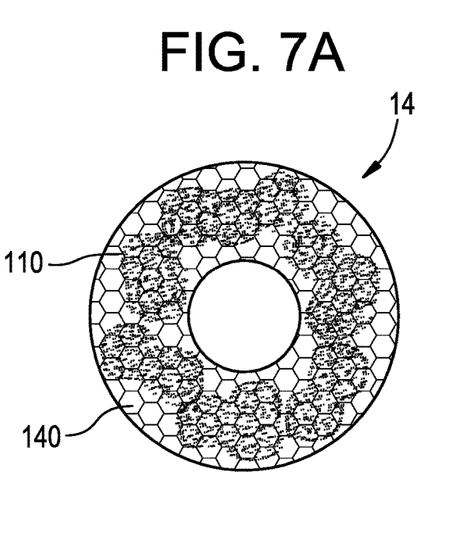
FIGS. 7A and 7B are cross sections of a reservoir of an e-vaping device that does not include a plurality of fibers.
Figure 7B:
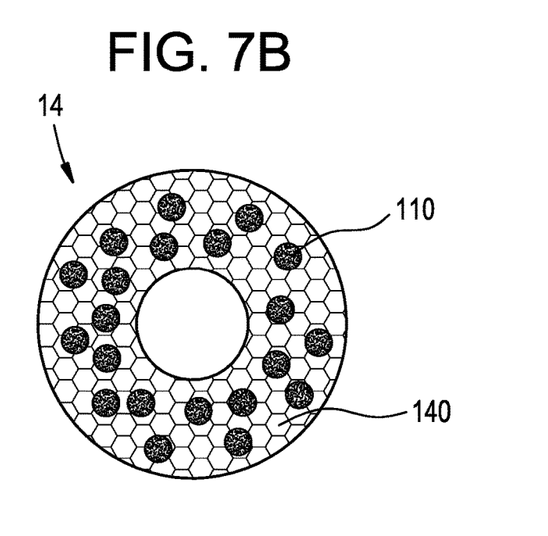

FIGS. 7A and 7B are cross sections of a reservoir of an e-vaping device that does not include a plurality of fibers. In FIGS. 7A and 7B, which are views of a radial cross-section of a reservoir 14' of an e-vaping device during operation of the e-vaping device. In FIG. 7A, which illustrates the state where the reservoir 14' is substantially full with the pre-vapor formulation solution 140, the pre-vapor formulation solution 140 is substantially homogeneously distributed in the gauze or other fibrous material 110. FIG. 7B illustrates a state where the pre-vapor formulation solution 140 has been used to a large extent and the reservoir 14' is substantially empty. As a result, the pre-vapor formulation solution 140 coalesces at one or more locations within the gauze 110. However, in the absence of the wringing effect created by the presence of fibers in the reservoir 14', residual amounts of the pre-vapor formulation solution 140 are not expelled from the gauze 110 and transferred to the wick (not shown) to be heated by the heater (not shown) and drawn out of the e-vaping device.

Figure 8:
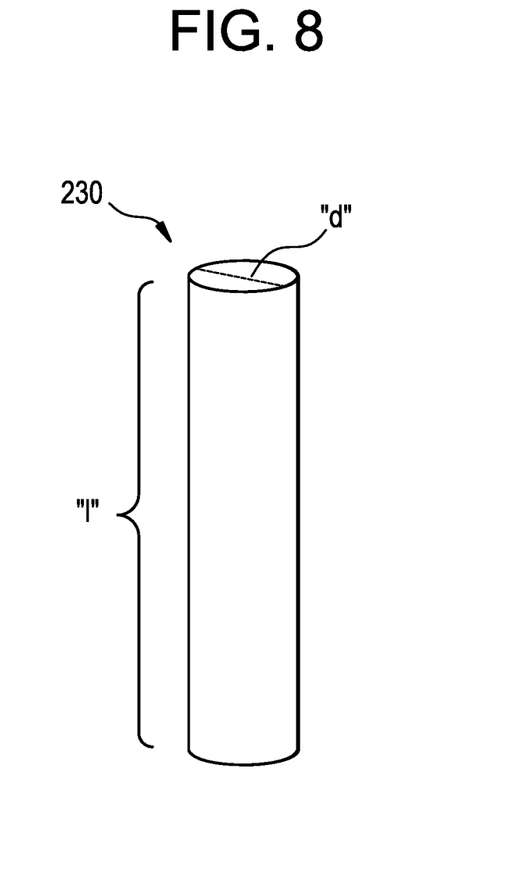
FIG. 8 is an illustration of a polymer fiber, according to at least one example embodiment.

FIG. 8 is an illustration of a polymer fiber, according to at least one example embodiment. In FIG. 8, the polymer fiber 230 may have a generally longitudinal shape with a diameter "d" and a length "l." In various example embodiments, the diameter "d" of the polymer fiber 230 may be in the range of about 20 μam to about 28 μm. Furthermore, in various example embodiments, the length "l" of the polymer fiber 230 may in the range of about 3 mm to about 7 mm. The surface areas of the fiber, which is the outer surface of the fiber, may be in a range of about 13 in$^2$ to about 17 in$^2$.

Example embodiments having thus been described, it will be obvious that the same may be varied in many ways. Such variations are not to be regarded as a departure from the intended spirit and scope of example embodiments, and all modifications as would be obvious to one skilled in the art are intended to be included within the scope of the following claims.

What is claimed is:

1. A cartridge configured to house a pre-vapor formulation for an e-vaping device, the cartridge comprising:
   an inner portion, including a heater and a wick; and
   an outer portion;
   wherein the outer portion includes a storage medium, the storage medium including
      a gauze configured to store the pre-vapor formulation, and
      a plurality of fibers dispersed in the gauze and configured to be mobile with respect to one another, the gauze and plurality of fibers being different fibers, the plurality of fibers being insoluble polymer fibers which are chemically inert in the presence of ingredients of the pre-vapor formulation; and
   wherein respective lengths of the plurality of fibers are in a range of about 3 mm to about 7 mm,
   the wick and the heater being configured to draw the pre-vapor formulation from the storage medium based on the heater being activated and vaporizing the pre-vapor formulation during operation of the e-vaping device.

2. The cartridge of claim 1, wherein the plurality of fibers are configured to be mobile with respect to one another based on the respective lengths of the plurality of fibers.

3. The cartridge of claim 1, wherein the respective lengths of the plurality of fibers are about 5 mm.

4. The cartridge of claim 1, wherein about 30% of the plurality of fibers have a length of about 3 mm, about 50% of the plurality of fibers have a length of about 5 mm, and about 20% of the plurality of fibers have a length of about 7 mm.

5. The cartridge of claim 1, wherein about 20% of the plurality of fibers have a length of about 3 mm, about 75% of the plurality of fibers have a length of about 5 mm, and about 5% of the plurality of fibers have a length of about 7 mm.

6. The cartridge of claim 1, wherein about 30% of the plurality of fibers have a length of about 3 mm, about 60% of the plurality of fibers have a length of about 5 mm, and about 10% of the plurality of fibers have a length of about 7 mm.

7. The cartridge of claim 1, wherein a surface area of each of the plurality of fibers is in a range of about 13 in$^2$ to about 17 in$^2$.

8. The cartridge of claim 7, wherein the surface area of each of the plurality of fibers is about 15 in$^2$.

9. The cartridge of claim 1, wherein the gauze is configured to configured to store the pre-vapor formulation.

10. The cartridge of claim 1, wherein the gauze and the plurality of fibers are configured to cooperatively wring the pre-vapor formulation from the storage medium, based on the plurality of fibers being free to move independently of each other.

11. A cartridge configured to house a pre-vapor formulation for an e-vaping device, the cartridge comprising:

an inner portion, including a heater and a wick; and
an outer portion;
wherein the outer portion includes a storage medium, the storage medium including
a gauze configured to store the pre-vapor formulation, and
a plurality of fibers dispersed in the gauze and configured to be mobile with respect to one another, the gauze and plurality of fibers being different fibers, the plurality of fibers being insoluble polymer fibers which are chemically inert in the presence of ingredients of the pre-vapor formulation; and
wherein a diameter of one or more of the plurality of fibers is in a range of about 20 μm to about 28 μm,
the wick and the heater being configured to draw the pre-vapor formulation from the storage medium based on the heater being activated and vaporizing the pre-vapor formulation during operation of the e-vaping device.

12. The cartridge of claim 11, wherein the diameter of one or more of the plurality of fibers is about 24 μm.

* * * * *